(12) United States Patent
Mason et al.

(10) Patent No.: US 8,718,335 B2
(45) Date of Patent: May 6, 2014

(54) BIOMETRIC AUTHENTICATION USING THE EYE

(75) Inventors: Stephen Archer Mason, Collaroy (AU); Edwin Jay Sarver, Carbondale, IL (US)

(73) Assignee: Wavefront Biometric Technologies Pty Limited, Sydney, NSW (AU)

( * ) Notice: Subject to any disclaimer, the term of this patent is extended or adjusted under 35 U.S.C. 154(b) by 159 days.

(21) Appl. No.: 12/742,405

(22) PCT Filed: Nov. 26, 2008

(86) PCT No.: PCT/AU2008/001744
§ 371 (c)(1),
(2), (4) Date: Aug. 26, 2010

(87) PCT Pub. No.: WO2009/067738
PCT Pub. Date: Jun. 4, 2009

(65) Prior Publication Data
US 2010/0310133 A1 Dec. 9, 2010

Related U.S. Application Data

(60) Provisional application No. 60/991,133, filed on Nov. 29, 2007.

(51) Int. Cl.
*G06K 9/00* (2006.01)
*H04N 7/18* (2006.01)

(52) U.S. Cl.
USPC ............................................ 382/117; 348/78

(58) Field of Classification Search
USPC ......... 382/112, 115, 117, 190, 116, 118, 124; 351/212; 623/4.1, 5.11, 5.15, 5.16, 623/906; 705/44, 67; 713/155, 161, 176, 713/186, 169; 348/78; 283/68, 78
See application file for complete search history.

(56) References Cited

U.S. PATENT DOCUMENTS

| | | | | |
|---|---|---|---|---|
| 6,356,649 | B2 * | 3/2002 | Harkless et al. | 382/115 |
| 8,265,375 | B2 * | 9/2012 | Shirley | 382/154 |
| 2008/0154524 | A1 * | 6/2008 | Shirley | 702/66 |

FOREIGN PATENT DOCUMENTS

| | | |
|---|---|---|
| JP | 62-232270 | 10/1987 |
| JP | 11-347016 | 12/1999 |

(Continued)

OTHER PUBLICATIONS

Halstead et al., "A Surface Algorithm for Reconstruction of corneal Topography from a Videokeratographic Reflection Pattern", Optometry and Vision Science, vol. 72, No. 11, Apr. 1995, pp. 821-827.

(Continued)

*Primary Examiner* — Abolfazl Tabatabai
(74) *Attorney, Agent, or Firm* — Snell & Wilmer L.L.P.

(57) ABSTRACT

This invention concerns apparatus and a method for authenticating a subject using their eye as an identifying biometric, in particular the shape of their cornea. The apparatus comprises an image projection device to generate and project an image of a pattern, made up of plural discrete points, onto at least a part of the cornea of an eye of the person. An image capture device to capture an image of the pattern of plural discrete points, after reflection in at least a part of the cornea of an eye of the person. And, a computer processor to extract a data set defining the locations of the discrete points in the captured image. The method comprises capturing an image of an illuminated pattern, made up of plural discrete points, after reflection in at least a part of the cornea of an eye of the subject. Comparing the locations of the discrete points in the pattern of the captured image against the locations of the discrete points in the pattern of a reference image. And, authenticating the identity of the subject depending on the similarity of comparison. In a further aspect the invention is software for performing the method.

21 Claims, 7 Drawing Sheets

(56) References Cited

FOREIGN PATENT DOCUMENTS

| | | |
|---|---|---|
| JP | 2000-187499 | 7/2000 |
| JP | 2000-222555 | 8/2000 |
| JP | 2001-231754 | 8/2001 |
| JP | 2004-178408 | 6/2004 |
| JP | 2006-244365 | 9/2006 |
| WO | WO 2006/101943 | 9/2006 |
| WO | WO 2007/097510 | 8/2007 |

OTHER PUBLICATIONS

PCT International Search Report and Written Opinion of the International Searching Authority, Australian Patent Office, Application No. PCT/AU2008/001744, Dec. 18, 2008, 8 pages.

* cited by examiner (a)            (b)

BIOMETRIC AUTHENTICATION USING THE EYE

This application claims priority from U.S. Provisional Patent Application No. 60/991,133 (Sarver and Mason) the contents of the specification of which are incorporated herein by reference.

TECHNICAL FIELD

This invention concerns apparatus and a method for authenticating a subject using their eye as an identifying biometric, in particular the cornea. In a further aspect the invention is software for performing the method.

BACKGROUND ART

The better known biometric markers currently used to identify people include analysis and comparison of facial features, irides, fingerprints, hand and palm prints, and wrist and finger pad blood vessels. Other biometric factors include analysis and comparison of gait, ear contour and DNA.

No one biometric parameter to date has proven to be perfectly accurate and practical across the entire human cohort. For example, the accuracy of facial feature recognition can vary significantly with changes in illumination. Five percent of the population has unreadable fingerprints, either being congenitally blurred or effectively removed through manual labour. In the United Kingdom, seven percent of the population failed to enroll in an iris recognition system. While DNA analysis is accurate, it is highly technical and there are generally lengthy delays before a result is known.

Another biometric that is highly unique and slowly time varying is the shape of the cornea—that is the dome like lens at the front of the eye. Currently the shape of the cornea is measured for clinical purposes using a corneal topographer; such as the Medmont E300 topographer. These machines use an illuminated series of concentric rings (known as a Placido disc) as a target source. One eye gazes directly at this illuminated target and an image is reflected from the pre-corneal tear film. By means of processing software, the reflected image is converted into a topographic map of the cornea representing the corneal contours.

U.S. 60/661,961 (Dixon et al) describes the use of gaze tracking and corneal 'surface irregularities' and 'discernable features' to define a unique biometric.

The use of the cornea as a biometric for identification is described in U.S. 60/685,484 (Mason). This system operates by capturing an image of at least part of the cornea and then deriving one or more 'geometric' parameters in respect to each of plural locations on the cornea; these parameters include measures of curvature, corneal height, refractive power, thickness and others. Authentication is then performed by comparing these parameters with previously derived parameters at the corresponding locations of a reference cornea.

DISCLOSURE OF THE INVENTION

In a first aspect the invention is an apparatus for authenticating a subject, comprising:

An image projection device to generate and project an image of a pattern, made up of plural discrete points, onto at least a part of the cornea of an eye of the subject.

An image capture device to capture an image of the pattern of plural discrete points, after reflection in at least a part of the cornea of an eye of the subject. And, A computer processor to extract a data set defining the locations of the discrete points in the captured image.

The same or another computer may be used to compare the data set defining the locations of the discrete points against the locations of the corresponding points of the pattern in a reference set; and to output an indication of whether the identity of the subject is authenticated or not.

The plural discrete points may be projected from a fixed array of point sources of light, for instance narrow beam LEDs. Alternatively, there may be a single light source that is distributed into the pattern; for instance using a mask or an arrangement of light guides.

The pattern of plural discrete points may be arranged in a regular formation along the intersections of concentric rings and radial lines, but no particular arrangement is necessary.

In addition to the plural discrete points there may be other elements in the reflected image. In particular a circular pattern may be projected from a ring light surrounding the aperture of the image capture means. Such a pattern may be useful for automatically determining that an eye is present and properly focused, and for locating the points in the image.

The pattern will ideally be projected onto the mid periphery of the cornea, but other regions such as the central region, far periphery and sclera may also be used.

The image capture device may comprise a telecentric lens and an image sensor. These are arranged, in use, coaxially with the cornea, and eye, of the subject. A chin rest or other aid may be provided to assist the user to position themselves appropriately.

An automatic focus device may be incorporated into the apparatus to ensure the image is properly focused before an image is captured. This device may require the subject's cooperation to achieve focus, for instance by adjusting the position or orientation of their head as information is fed back to them. In any event the computer may be used to automatically determine when proper focus is achieved.

The computer processor will typically also control the lights and camera. The lights will be automatically turned ON and OFF at appropriate times during the authentication process, and the camera will be controlled to capture images at appropriate times.

In addition the intensity of the lights may be varied when they are ON, either all together or each light independently. Such "twinkling" of the lights adds another degree of freedom to the procedure that makes it harder to subvert and can provide more robust image processing results.

Authentication is generally required at a range of different places, and since security may be compromised by replication of reference data sets, a central secure reference repository may be used to store them securely. In this scenario image data sets extracted by the apparatus will be encrypted and sent to the repository where the comparison and authentication will take place. The result of the authentication may be returned to the local processor where it may be displayed to an operator. Alternatively the result may be used to automatically control equipment; such as opening a secure door in the event of a positive authentication or activating an alarm if authentication fails.

Where authentication is performed remote from the image capture, then a range of security measures may be required to ensure the integrity of the resulting determination, including public key encryption and a maximum permissible turn-around time.

In a second aspect the invention is a method for authenticating a subject, comprising the steps of:

Capturing an image of an illuminated pattern, made up of plural discrete points, after reflection in at least a part of the cornea of an eye of the subject.

Comparing the locations of the discrete points in the pattern of the captured image against the locations of the discrete points in the pattern of a reference image. And, Authenticating the identity of the subject depending on the similarity of comparison.

The reflected image of the pattern is unique for each subject, as a result of the unique shape of the cornea which is not perfectly spherical, imparting distortion, or coding, to the pattern reflected in it.

In fact reflection occurs in the pre-corneal tear film, and without this overlaying tear film the corneal epithelium would not accurately transmit light for clear vision. The tear film, despite constantly changing before, during and after the blinking process, is an almost precise duplication of the corneal morphology upon which it rests. Light reflected from the cornea in this way is known as the First Purkinje Image(s), and it is this image that is captured.

The method typically involves specular reflection of the pattern in at least part of the cornea.

The image capture step may involve capturing two images, one with the lights OFF and the other with the lights ON. Subtraction of one of these images from the other results in the elimination of stray light.

Authentication relies upon a direct comparison between the locations of the discrete points in a currently captured image and one or more previously obtained reference images. For instance a single reference image could be captured at a registration event for the same subject. Alternatively, a series of reference images of a variety of subjects, including the present subject, could be used for comparison.

The method may include the further step of extracting a data set defining the locations of the discrete points in the captured image.

The data set could comprise simply the locations measured in Cartesian (X, Y) or polar (r, θ) coordinates in the current image and the reference image(s). Alternatively, the data set could comprise a difference (δ) between the locations and the original pattern or the original pattern after reflection in a reference sphere. A reference sphere having a radius of 7.8 mm may be used for this purpose.

The comparison itself may involve a selected degree of sensitivity, for instance the tolerance of measurements of the locations in either the current or the reference images, or both, may be selected according to the degree of certainty required by the authentication process. This allows inexpensive equipment to operate very quickly in low security situations, or for screening. However, much more stringent authentication criteria may be employed for, say, access to high security locations.

The comparison may involve the use of different weightings applied to different points of the pattern. In particular points further from the centre of the pattern may be given more weight in the comparison calculation.

In an additional step, authentication may be denied when there is an exact match between the current record set and the reference set. This may seem curious, but there are very small changes occurring all the time in the shape of the pre-corneal tear film, and so a match with a difference value too small may indicate that fraudulent data has been provided.

It will be appreciated that the invention compares the effect of the shape of the cornea upon the locations of a known pattern of points, rather than parameters representing the geometry of the cornea calculated at a series of locations on the corneal surface, as in U.S. 60/685,484 and U.S. 60/661, 961. These earlier documents presuppose the use of a corneal topographer which automatically calculates a range of geometric parameters and makes them available for use. However, the present invention does not rely upon use of such sophisticated equipment, or the complex calculations it performs. Instead very simple equipment may be used to obtain relatively small amounts of data that can be processed with great rapidity to provide a reliable authentication test.

The subjects will typically be people, but there is no reason why the technique could not be applied to other animals, such as to authenticate the identity of racehorses.

In a further aspect the invention is software, that is machine readable code on a machine readable medium, for controlling the apparatus to perform the method. The machine readable medium is preferably a non-transitory computer-readable medium that includes, but is not limited to, non-volatile memory and volatile memory, such as, hard drives, compact discs, floppy discs, flash memory, ROM, RAM, but does not include a transitory signal per se.

BRIEF DESCRIPTION OF THE DRAWINGS

An example of the invention will now be described with reference to a Corneal Specular Reflex Authentication (CSRA) system and the accompanying drawings, in which.

BEST MODES OF THE INVENTION

Figure 1:
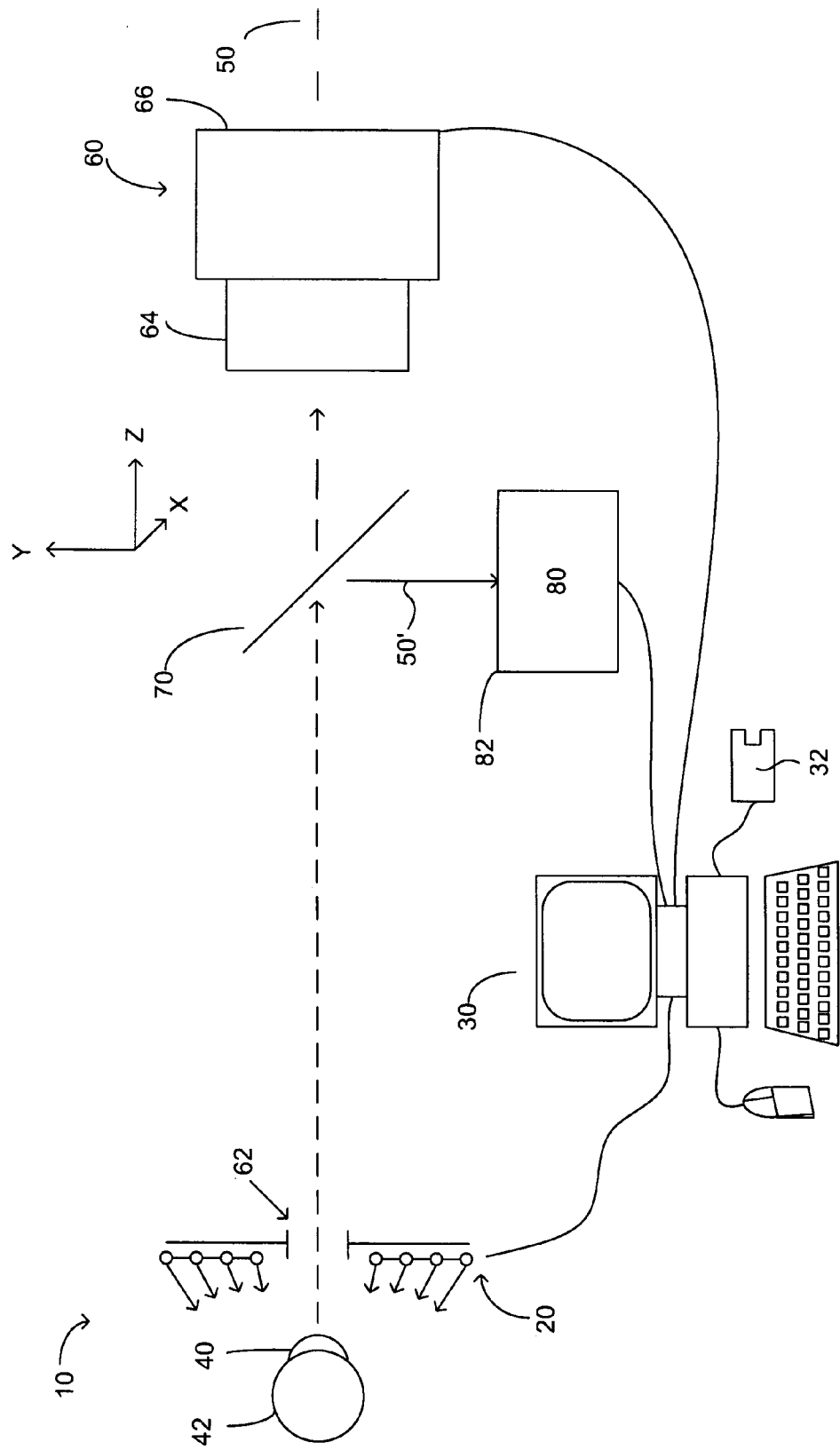
FIG. 1 is a block diagram of the basic layout of the Corneal Specular Reflex Authentication (CSRA) system.

Referring now to FIG. 1 the Corneal Specular Reflex Authentication (CSRA) system 10 comprises a pattern of target lights 20 controlled by a computer 30 to selectively project an image of the target lights onto the cornea 40 of the eye 42 of a subject that is aligned with the axis 50 of a camera system 60.

The camera system 60 comprises an optical aperture 62, a telecentric lens 64 and an image sensor 66 aligned along the optical axis 50.

A beam splitter 70 is also located on the axis 50 behind the aperture 62. The beam splitter 70 is positioned at 45° with respect to axis 50 to reflect some of the light travelling along the axis to a self alignment aid 80.

The System

The elements of the system will now be described in greater detail with reference to FIGS. 1 to 4.

Figure 2:
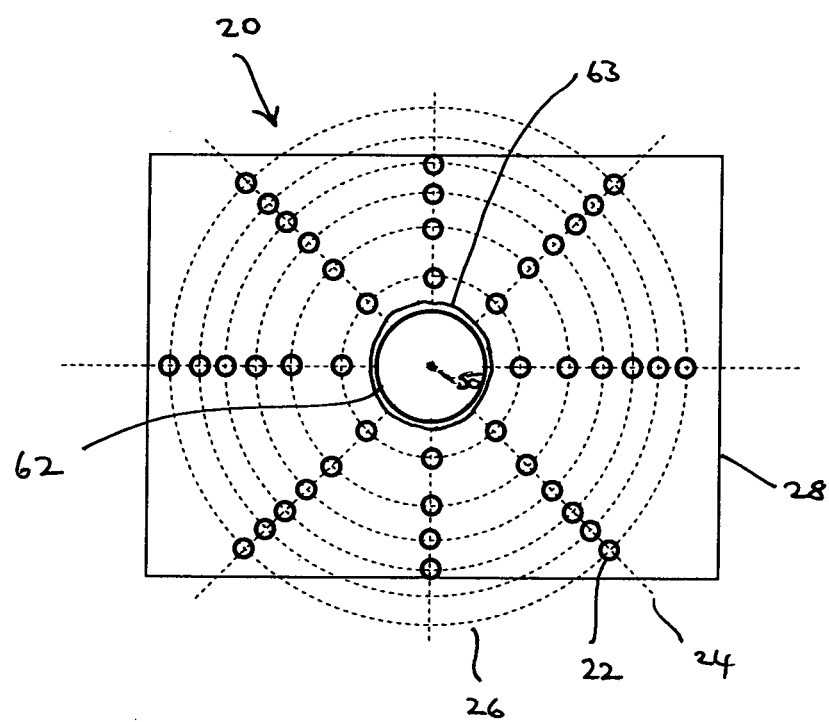
FIG. 2 is a diagram of a polar arrangement of target lights.

Referring first to FIG. 2 the target lights 20 comprise forty-eight point light sources 22 arranged in a pattern defined by the intersection of virtual lines 24 radiating from axis 50 and virtual concentric circles 26 around the axis 50. The lights are also confined to lie within a rectangular boundary 28.

It will be appreciated that the coding imparted to the image will be averaged over the area of each point reflected in the cornea. It follows that if the footprint of the points is too large, that is covers too large an area of the cornea, then the information about the shape of the cornea coded into the resulting image will be degraded. In general the size of the points is determined by the size of the point light sources, their distance from the cornea and the degree of dispersion of the beams they project. Depending on the degree of security required some trial and error may be necessary to configure these variables appropriately when designing a particular system.

The point light sources 22 in this example are visible light emitting diodes (LEDs) with a diameter of 5 mm and a narrow circular forward beam, or no lens. Smaller sized LEDs will still work provided they can be adequately imaged after reflection. Very large or diffuse LEDs may have to be further away from the eye, otherwise the footprint of their reflection on the cornea might be too large for accurate coding by the cornea surface. Alternatively, the light sources could be implemented as a back lit panel with holes arranged in the pattern.

In any event, the light sources 22 are positioned, and the pattern arranged, to reflect off a standard size (reference) cornea (a 7.8 mm radius sphere); with the innermost lights reflecting on a 2 mm diameter circle centered on the corneal vertex, and the outermost lights reflecting horizontally on a 6 mm diameter, and vertically on a 5 mm diameter.

The optical aperture 62 accepts light indirectly from the target lights 20 after reflection in the cornea 40. Aperture 62 is surrounded by a ring light 63 comprised of a ring of side-emitting optical fibre. The purpose of the ring light 63 is to simplify the process of finding the center of the reflected pattern of target lights in the digitized image as well as aid the user in aligning their eye 42 with the system axis 50. These functions are explained below.

The pattern of lights 20 and the light ring 63 are switched ON and OFF under control of the computer 30. Status information concerning the lights is returned to the computer. The computer may be a local computer or a remote server. In either case it may be networked together to share local information with a central computer.

The computer is programmed to control the process for the operator or subject so that a suitable image is captured, and to perform the near real time calculations required for authentication. The computer may also deliver the result or take some other action, such as releasing a lock, depending upon whether authentication is confirmed, or not.

The telecentric lens 64 of the camera system 60 focuses the image of the target lights 20 reflected off the cornea 40 onto the camera sensor 66. The advantage of a telecentric lens is that slight changes in the distance from the cornea's vertex to the image sensor 66 will not result in a change in the size of the reflected pattern.

Figure 3:
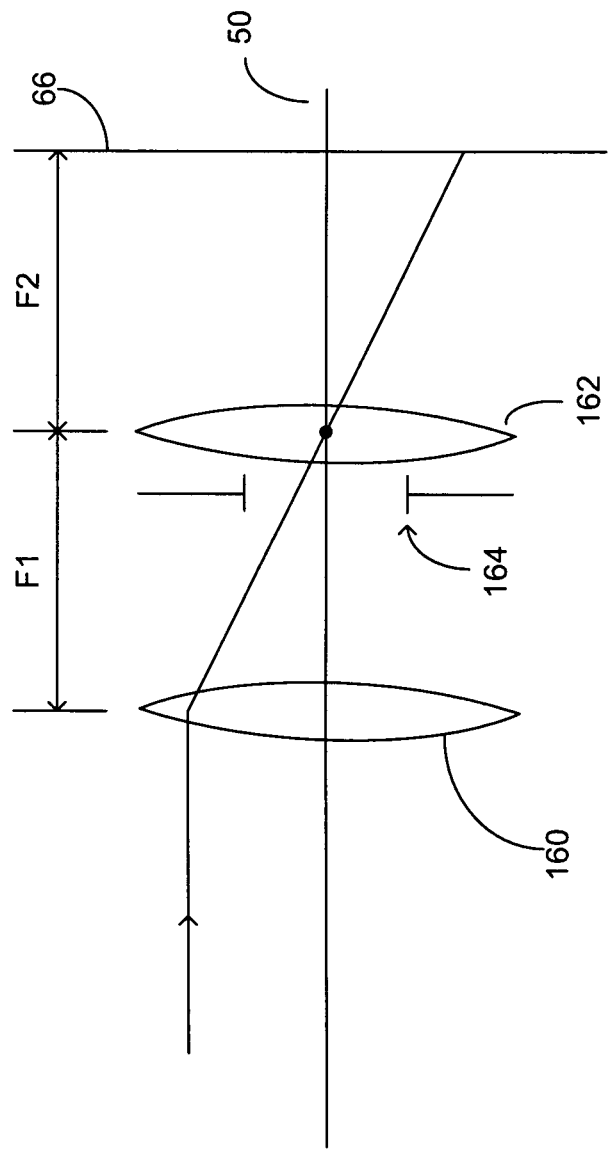
FIG. 3 is an optical diagram of a telecentric camera lens.

The basic configuration of a telecentric camera lens 64 is illustrated in FIG. 3. In this configuration, there are two lenses 160 and 162. A light ray parallel to the system axis 50 incident at the first lens 160 will cross the axis at a distance determined by the focal length F1 of the lens. At this location there is an aperture 164 immediately in front of second lens 162. The light transmitted through second lens 162 is brought into focus at a distance given by its focal length F2.

The image sensor 66 is placed at this point of focus. The magnification of the lens is established from the ratio of the focal lengths of lenses 160 and 162. By selecting the diameter of aperture 164 to be small, say 3 mm, only parallel rays are brought into focus at the plane of the camera sensor 66. In this way the telecentric configuration keeps the height of reflected target lights relatively constant regardless of small discrepancies in the distance between the user and the sensor 66.

The image sensor 66 digitizes the image using a monochrome CCD or CMOS sensor array. A digital interface such as USB 2 connects the output of the sensor array to computer 30. The image captured by the sensor 66 is the reflection of the pattern of target lights 20 in the surface of the subject's cornea 40. In fact the image is reflected from the tear layer; it is known as the first Purkinje image. The image also includes the reflection of the light ring 63 that surrounds aperture 62 when it is illuminated.

The beam splitter 70 allows light passing through aperture 62 to travel along axis 50 to the camera system 60. In addition beam splitter 70 provides a proportion of the light to the alignment aid 80. This aid simply reflects light in a cross hair at surface 82 back along its path of arrival, and it is reflected by beam splitter 70 to be viewed by the user. The cross hair is simply marked onto the reflecting surface 82 and centered on axis 50' which is axis 50 after reflection down to surface 82 by beam splitter 70.

Figure 4:
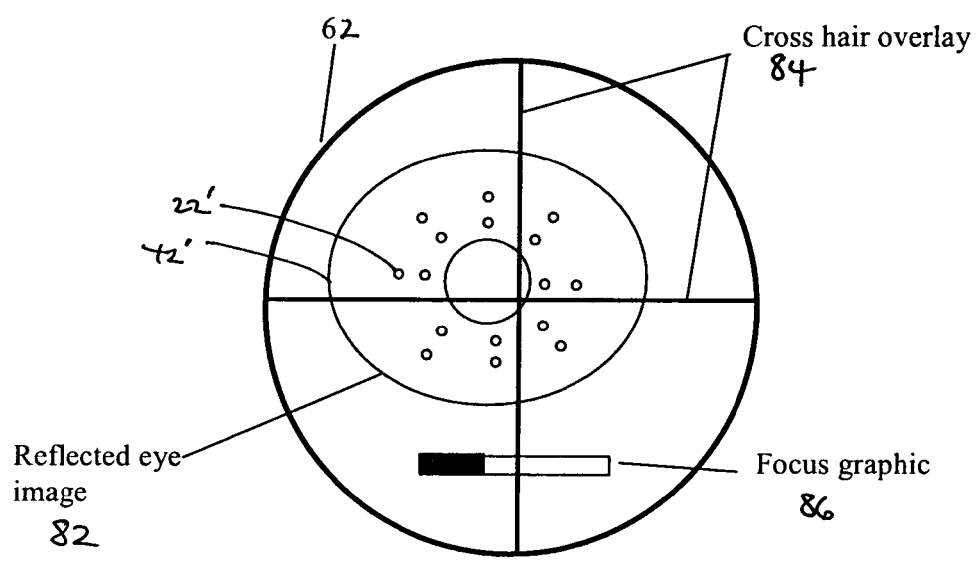
FIG. 4 is a diagram of the self-alignment image seen by user before authentication.

The image seen by the user through aperture 62 is shown in FIG. 4. If the axis of eye 42 were perfectly aligned with the optical axis 50 then the user would see the reflection of their eye perfectly centered in the cross hair 84. However, in the example shown the reflected eye 42' is not perfectly aligned, but is seen to be slightly to the left (X-direction) and slightly high (Y-direction) compared to the centre of the cross hairs. The user is asked to move their head until their eye is properly centered before an image is captured.

Note also in FIG. 4 the pattern of target lights reflected by the cornea 22' as well as a focus graphic 86 which is generated by alignment aid 80, and projected back to the user via reflection in beam splitter 70. The focus graphic 86 helps the user align in the Z (axial distance) direction. The focus graphic 86 provides feedback regarding how well the image is in focus at the image capture plane 66. In this case focus graphic 86 is shown as a bar graph that moves in real time under the control of signals from computer 30. The bar responds instantaneously to feedback from the camera system 60 regarding the state of focus of the current captured image.

The Method

Figure 5:
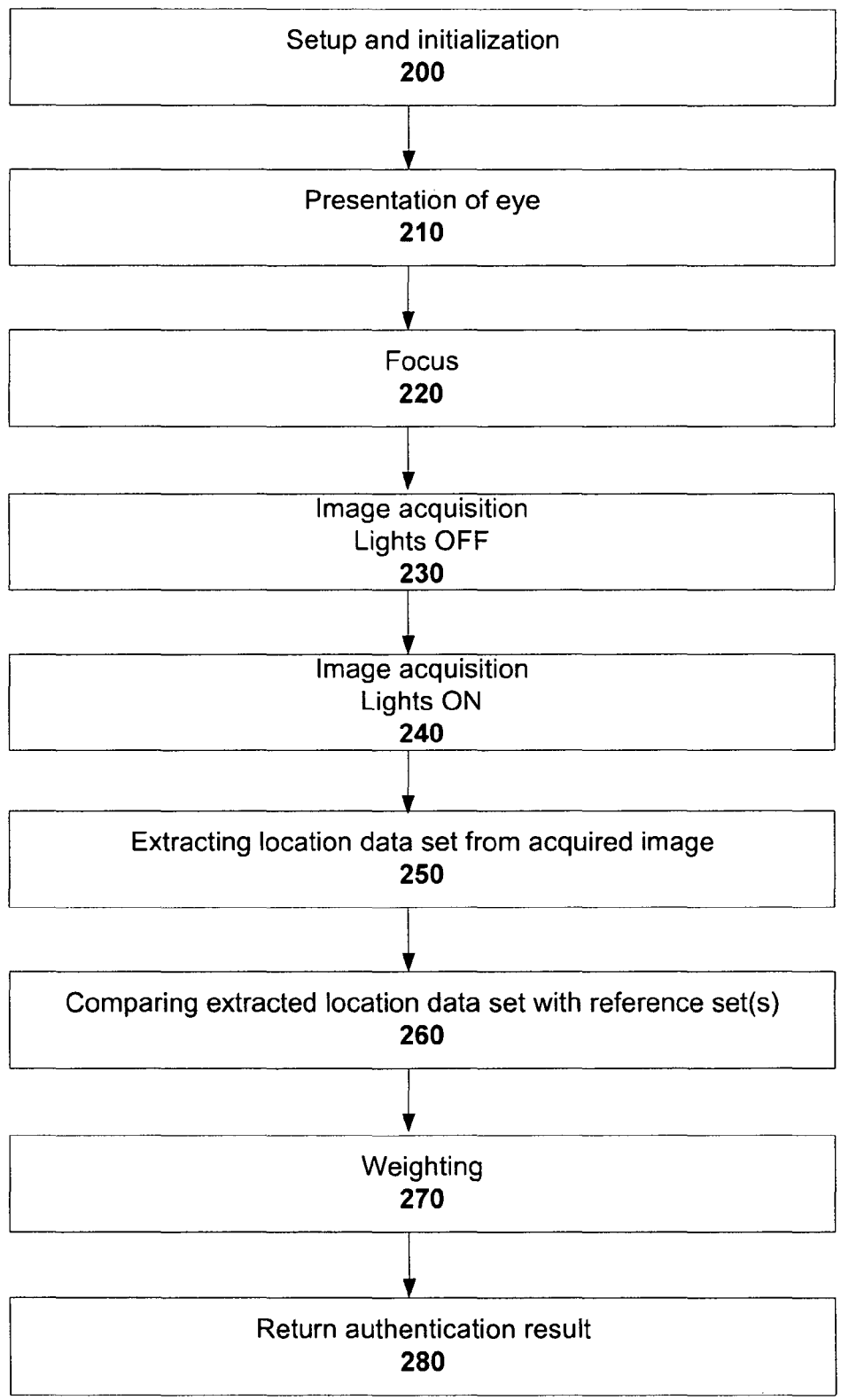
FIG. 5 is a flow chart of the authentication process.

Use of the system for authentication will now be described with reference to FIG. 5.

After the CSRA system has been set up and turned on, operation commences with an operator or subject initiating authentication of the subject 200 at the computer 30. The computer's keyboard is used to provide, for instance, the following information: the subject's name, identification number, and information regarding target point reflection locations for the user's cornea. A separate input device 32 may be connected to the computer 30, such as a card reader, to read for instance to read this information from the subjects identity card.

The subject then presents their eye 42 to the system 210, for instance by standing or sitting in front of the target lights 20, and gazing directly toward the centre of the pattern 20.

The operator, or a voice or other audible signal generated from the computer, then instructs the subject to move their head until their eye 42 is in the correct location, and the image of the cornea in the image capture plane 66 is properly focused 220.

There are two steps in reporting the focus state of the digitized eye image. First, is to determine if an eye image is present 245. Second, is to calculate the focus measure 250 and report it.

To determine if an eye image is present, an image is captured using camera system 60 with the ring light 63 ON. The captured image is then analysed by computer 30 to identify a properly centered and sized ring corresponding to the illuminated system aperture ring light 63.

Given the expected range of corneas to be measured (that is a central radius of curvature between 6.00 mm and 10.00 mm), the optical magnification of the camera lens 64, and the camera sensor element size 66, then the expected range in size of the illuminated central ring feature 63 can be predicted. This predicted feature is cross-correlated with the image data and the maximum cross-correlation is found, which locates the expected centre of the eye, if present.

Once the expected center of the eye is found, the magnitude of the correlation value is compared to a threshold T1. If the correlation value is above the threshold value T1, a search is performed on the image in a set of radial directions from the centre peak outward for the occurrence of the first bright pixel. The location of each of these pixels forms a contour that is fitted to an ellipse equation. The major and minor diameters of the ellipse are compared to the expected range of reflected circle sizes. If the calculated major and minor diameters are within the range of threshold values T2 and T3, the system defaults to the assumption that the found contour is in fact the image of the aperture ring 63 reflected in a cornea.

If the major or minor diameters are outside the range, or the initial correlation value is below T1, the system defaults to the assumption that the contour is not for the reflected aperture ring on the cornea, and that no eye is present, and so no further processing is performed.

A focus measure F is used to give an estimate of how well the captured image is focused. There are several suitable methods for performing this task. Due to its performance and simplicity, we have selected the focus measure calculated in Equation (1):

$$F = \sum_R |4I(i, j) - I(i-1, j) - I(i, j+1) - I(i+1, j) - I(i, j-1)| \quad (1)$$

Where, the sum is over a region R calculated for the captured image toward the center or mid-periphery of the image.

The image pixel values are represented by the two-dimensional array I(i,j). And, The state of focus is summarized by the following:
If F<T4 then image is not focused.
If T4<F<T5 then image is marginally focused
If F>T5 then the image is focused
The threshold values T4 and T5 are set at values dependent upon the CSRA system application, the population being measured and the environment in which the system is placed. Once the focus value is determined, the actual focus status is indicated to the user via the focus graphic 86.

After a suitably high focus value F has been found for an image, the software will save the best focused image and automatically proceed with further image processing to determine authentication. When the software moves into this state, the system will indicate to the subject that they are no longer required to present their eye for evaluation. Before doing so an image of the eye is acquired with the target lights 20 and ring light 63 OFF. By subtracting this image from the image acquired with the lights ON stray light, such as the reflection of room lights from the cornea, is eliminated from subsequent calculations.

Further processing to determine authentication requires the precise locations of the reflected pattern of target points 20' to be extracted 250 from the image.

Figure 6:
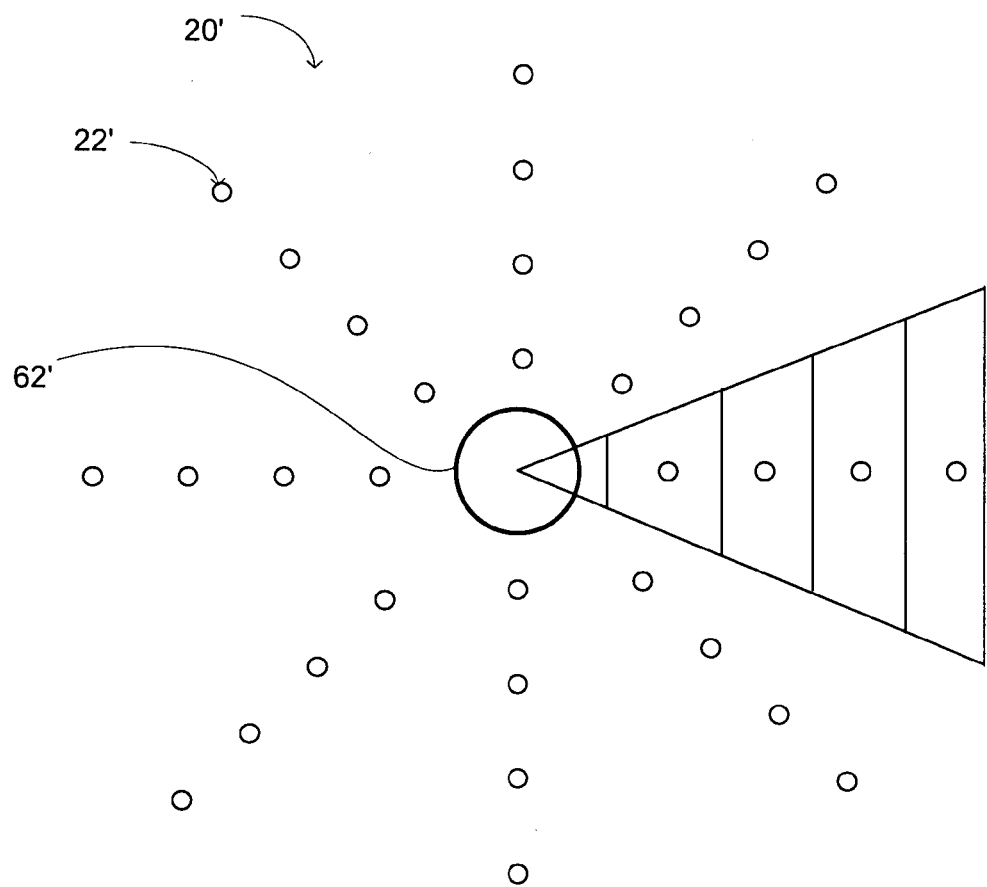
FIG. 6 is a diagram illustrating part of the process for determining the location of the points in the image.

Since the image of the central aperture ring 62' has already been found, the system knows where the reflected target point pattern 20' is centered. The pattern scale factor is estimated from the image of the central aperture ring 62' and then the expected location of each discrete specular reflection is determined. A series of virtual boxes 90 are positioned around the expected locations of the reflected points 22' of the reflected pattern 20', as seen in FIG. 6. Further process is confined to the regions within these boxes 90.

Figure 7:
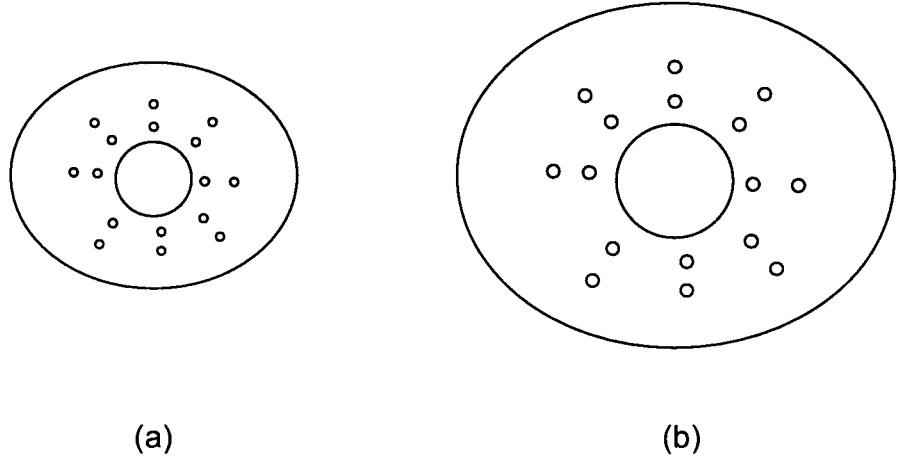
FIG. 7 is a pair of diagrams illustrating the effect of a smaller radius of curvature (a), and a larger radius of curvature (b), of the cornea on the reflected pattern.

For relatively small corneas (having less than average radius of curvature), the points will tend to be grouped closer to the center of the central aperture, as seen in FIG. 7(*a*). For relatively large corneas (having greater than average radius of curvature), the points will tend to be spread out further from the central aperture, as seen in FIG. 7(*b*).

Prior to searching each region bounded by a box 90, the entire image is made smooth using a 3×3 box averaging filter to reduce noise in the image. Then, each region 90 is searched for the brightest sample. This brightest sample is taken to be near the centre of the point. The centroid is then computed for the 5×5 pixel neighborhood around the centre to obtain a sub-pixel estimate of the true location of the reflected target point 22'. If the brightest sample in a region is below a threshold T6, the system declares that the point is missing. Once the target point region has been processed, an array is updated with the (X, Y) pixel location of the point (relative to the center of the central aperture ring). The entry (−1,−1) is used to indicate that the point is missing.

Once the central aperture ring and reflected target points are located, the software is ready to determine a score of similarity between the current location data set and one or more sets of reference location data 260. In general the score of similarity between two sets of data is computed according to equation (2):

$$M = \frac{\sum_{n \in N} w_n |A_n - B_n|^p}{\sum_{n \in N} w_n} \quad (2)$$

Where, M is the match score between location data set A and location data set B. N is the set of locations that are NOT (−1,−1). That is, N is the set of valid locations for both A and B.

The weights w are used to allow points further out from the center of the pattern to be given more importance than points closer to the center 270. The weights are used to represent the area surrounding each point or the expected accuracy of a point. The parameter p is an integer greater than 0.

When the score computed using equation (2) is greater than a given threshold T7 then the subject is authenticated; and if not then not 280.

For large data sets, two-dimensional data filtering is performed. First, the average central aperture ring diameter is used. Then, the ellipse ratio (minor diameter/major diameter) of the image of the ring is used. In this way, database searches can be limited to records that have images of the central aperture rings with similar dimensions and shapes.

An alternative is to compare the current subject against a cohort of other subjects as well as their own earlier records, retrieved using their nominated identity. The closest match to the current data set, provided it is labeled with the same identity, will authenticate the subject.

The Software

The CSRA system is essentially controlled by software residing in computer 30 of FIG. 1.

The main functions of this software are:
Interfacing with the computer's input devices.
Interfacing with the lights and camera.
Determining eye presence and alignment.
Determining the focus state.
Processing reflected images to extract data sets.

Calculating authentication scores.

Communicating the authentication result, and possibly controlling other equipment in response.

INDUSTRIAL APPLICATION

There are many uses for effective authentication systems, and here we list a number of applications for which the current system is particularly suited:

- Healthcare, for example, patient identification, particularly if they are old, demented, or unconscious for instance immediately before surgery.
- Banking, for example at ATM's, or personnel/staff identification
- Airline pilots/public transport drivers, for example to activate controls only when registered pilots are identified as present.
- Military, all areas requiring personnel identification.
- High security access, for banks, prisons and consulates.
- Low security access, for residential buildings and schools.
- Pharmacies, for accessing restricted drugs, such as methadone.
- Internet chat rooms, to identify and screen users.
- Social Security, to address fraudulent payment of benefits.
- Animal Identification, for example, identification of thoroughbred horses or any other valuable animal. Or animals registered for showing such as dogs, cats and cattle. The technique could also assist in the control of transmissible diseases such as Bovine Spongiform Encephalitis, by identify cattle for slaughter.

Although the invention has been described with reference to particular examples and aspects it should be appreciated that it is not limited to these arrangements. For instance:

- Any other suitable pattern of lights could be used.
- Any other suitable layout of the apparatus could be used.
- A different alignment aid could employ a small light that was only visible when the subject's eye was properly aligned.
- A different focus indicator could be used, such as changing colors that indicate focus being acquired as the colours change from red, to yellow to green.
- Alternatively again, audible feedback could be provided.
- The weights used in the comparison could be optimized for the application to increase the reliability of the authentication.
- An adaptive optimisation process could be employed.
- Finally alternative methods of data analysis could be performed before the comparisons step. These might include Zernike Polynomial analysis, Fourier analysis or Karhunen-Loeve transforms applied to the data obtained from the discrete corneal specular reflections.

The invention claimed is:

1. Apparatus for authenticating a subject, comprising:
an image projection device to generate and project an image of a pattern, made up of plural discrete points, onto at least a part of the cornea of an eye of the subject;
an image capture device to capture an image of the pattern of plural discrete points, after reflection in at least a part of the cornea of an eye of the subject; and,
a computer processor to extract a first data set defining the locations of the discrete points in the captured image, and to compare the first data set against a second data set defining locations of corresponding points in a reference set according to:

$$M = \frac{\sum_{n \in N} w_n |A_n - B_n|^p}{\sum_{n \in N} w_n}$$

where M is a similarity score between the first data set and the second data set, N is the set of valid locations for both the first dataset and the second dataset and w are weights used to allow points further from a center of the pattern to be given more weight in the similarity score M than points closer to the center, and the parameter p is an integer greater than zero.

2. Apparatus according to claim 1, wherein the computer is further used to output an indication of whether the identity of the subject is authenticated or not based on the comparison.

3. Apparatus according to claim 1, wherein in addition to the plural discrete points there are other elements in the reflected image.

4. Apparatus according to claim 3, wherein the other elements are used to automatically determine that an eye is present and properly focused.

5. Apparatus according to claim 1, wherein the image capture device comprises a telecentric lens and an image sensor arranged, in use, coaxially with the cornea, and eye, of the subject.

6. Apparatus according to claim 1, wherein an alignment device is incorporated into the apparatus to ensure the subject's eye is properly aligned before an image is captured.

7. Apparatus according to claim 1, wherein an automatic focus device is incorporated into the apparatus to ensure the image is properly focused before an image is captured.

8. Apparatus according to claim 1, wherein the intensity of the lights is varied when they are ON, either all together or each light independently.

9. Apparatus according to claim 1, in combination with a remote secure reference repository and a secure communications link between them.

10. A method for authenticating a subject, comprising the steps of:
capturing an image of an illuminated pattern, made up of a first set of plural discrete points, after reflection in at least a part of the cornea of an eye of the subject;
comparing locations of the first set of plural discrete points in the pattern of the captured image against the locations of a second set of plural discrete points in the pattern of a reference image according to:

$$M = \frac{\sum_{n \in N} w_n |A_n - B_n|^p}{\sum_{n \in N} w_n}$$

where M is a similarity score between the first data set and the second data set, N is the set of valid locations for both the first set and the second set, w are weights used to allow points further from a center of the pattern to be given more weight in the similarity score M than points closer to the center, and the parameter p is an integer greater than zero; and,
authenticating the identity of the subject depending on the similarity of comparison.

11. A method according to claim 10, wherein the image is captured after specular reflection of the pattern.

12. A method according to claim 10, wherein the image capture step involves capturing two images, one with the pattern illuminated and the other with the pattern not illuminated.

13. A method according to claim 10, wherein authentication relies upon a comparison between the locations of the first set of discrete points in a currently captured image and the locations of the second set of discrete points of one or more previously obtained reference images.

14. A method according to claim 10, wherein authentication relies upon a comparison between the locations of the first set of discrete points in a currently captured image and the locations of the second set of discrete points of a series of reference images of a variety of subjects, including the present subject.

15. A method according to claim 10, including the further step of extracting a data set defining the locations of the first set of discrete points in the captured image.

16. A method according to claim 10, wherein the locations are represented in Cartesian (X, Y) or polar (r, θ) coordinates in the current image and the reference image(s).

17. A method according to claim 10, wherein the locations are represented as a difference (δ) between the location measured and the original pattern or the pattern after reflection in a reference surface.

18. A method according to claim 10, wherein the comparison involves measurements of either the current or the reference images, or both, at a degree of accuracy required by the authentication process.

19. A method according to claim 10, wherein the comparison involves the use of different weightings (w) applied to different points of the pattern.

20. A method according to claim 10, comprising the further step of denying authentication when there is an exact match between the locations of the first set of discrete points in the current image and the locations of the second set of discrete points in the reference image.

21. A non-transitory computer-readable medium that provides instructions, which when executed by a computer, cause the computer to perform the operations of claim 10.

* * * * *